US00PP27135P3

(12) United States Plant Patent
Klemm et al.

(10) Patent No.: US PP27,135 P3
(45) Date of Patent: Sep. 6, 2016

(54) POINSETTIA PLANT NAMED 'NPCW14221'

(50) Latin Name: *Euphorbia pulcherrima*
Varietal Denomination: NPCW14221

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 118 days.

(21) Appl. No.: 14/544,328

(22) Filed: Dec. 23, 2014

(65) Prior Publication Data

US 2016/0183436 P1 Jun. 23, 2016

(51) Int. Cl.
*A01H 5/02* (2006.01)

(52) U.S. Cl.
USPC ..... Plt./307

(58) Field of Classification Search
USPC ..... Plt./307
See application file for complete search history.

(56) References Cited

PUBLICATIONS

UPOV hit on QZ PBR 20143340 Dec. 11, 2014.*
UPOV hit on CA 14-8505 Dec. 19, 2014.*

* cited by examiner

*Primary Examiner* — Anne Grunberg
(74) *Attorney, Agent, or Firm* — Barbara Campbell; Bethany R. Roahrig; Cochran Freund & Young, LLC

(57) ABSTRACT

A new poinsettia plant particularly distinguished by having dark red bracts, dark green foliage, and a late flowering time, is disclosed.

1 Drawing Sheet

Genus and species: *Euphorbia pulcherrima.*
Variety denomination: 'NPCW14221'.

BACKGROUND OF THE NEW PLANT

The present invention comprises a new and distinct variety of poinsettia, botanically known as *Euphorbia pulcherrima* and hereinafter referred to by the variety name 'NPCW14221'. 'NPCW14221' was derived as a selection from a cross-pollination conducted in Nairobi, Kenya in November/December 2008 between the proprietary female parent 'EP-1995-0002' (unpatented) and the proprietary male parent 'EP-1995-0001' (unpatented).

In October 2009, a single plant was selected in Stuttgart, Germany from plants produced from the initial cross. In May 2010, 'NPCW14221' was first asexually propagated by vegetative apical cuttings. 'NPCW14221' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Dark red bracts;
2. Dark green foliage; and
3. A late flowering time.

DESCRIPTION OF THE PHOTOGRAPH

This new poinsettia plant is illustrated by the accompanying photograph which shows an overall view of the whole plant. The photograph is of a plant approximately four-months-old grown indoors in Stuttgart, Germany in November 2012.

The colors shown are as true as can be reasonably obtained by conventional photographic procedures.

DESCRIPTION OF THE NEW VARIETY

The following detailed descriptions set forth the distinctive characteristics of 'NPCW14221'. The data which define these characteristics were collected from asexual reproductions carried out in Stuttgart, Germany. Data was collected on plants 19-weeks-old after potting grown in a greenhouse in Stuttgart, Germany under greenhouse conditions in November 2012. Color references are to The R.H.S. Colour Chart of The Royal Horticultural Society of London (R.H.S.), $5^{th}$ edition (2007).

Classification:
- *Family.*—Euphorbiaceae.
- *Species.*—*Euphorbia pulcherrima.*
- *Common name.*—Poinsettia.
- *Variety.*—'NPCW14221'.

Parentage:
- *Female.*—Proprietary poinsettia parent 'EP-1995-0002' (unpatented).
- *Male.*—Proprietary poinsettia parent 'EP-1995-0001' (unpatented).

Growth:
- *Blooming habit.*—Intermittent.
- *Flowering response time.*—Approximately 60 days.
- *Keeping quality.*—Excellent.

Plant description:
- *Form.*—Triangular.
- *Growth habit.*—Upright.

*Height.*—28.0 cm to 30.0 cm.
*Width.*—23.0 cm to 28.0 cm.
*Number of branches.*—6.
*Average number of inflorescences per plant.*—6.

Propagation:
*Type cuttings.*—Apical cuttings.
*Time to produce a rooted cutting.*—4 weeks.

Stems:
*Color.*—RHS 143A is the main color with RHS 60A spots and stripes on parts of the stems.
*Length.*—25.0 cm.
*Internode length.*—1.0 cm to 3.0 cm.
*Diameter.*—0.5 cm to 0.8 cm.

Leaves:
*Quantity.*—6 to 7 per lateral branch.
*Arrangement.*—Alternate.
*Shape.*—Ovate.
*Apex.*—Acute.
*Base.*—Obtuse.
*Margin.*—Serrate.
*Length.*—10.0 cm to 12.0 cm.
*Width.*—7.0 cm to 9.0 cm.
*Lobe characteristics.*—Shallow.
*Texture (both surfaces).*—Smooth.
*Vein color.*—Upper surface: RHS 60A for the middle vein and transparent for the other veins. Lower surface: RHS 53A for the middle vein and RHS 139D for the other veins.
*Variegation.*—Absent.
*Color.*—Mature foliage: Upper surface: RHS 136A. Lower surface: RHS 136B. Immature foliage: Upper surface: RHS 141A. Lower surface: RHS 139B.
*Leaf petiole.*—Length: 3.0 cm to 5.0 cm. Diameter: 0.2 cm to 0.3 cm. Color: Upper (part) surface: RHS 47A. Lower (part) surface: RHS 53B.

Inflorescence:
*Lastingness of inflorescence on the plant.*—4 weeks.
*Diameter.*—23.0 cm to 28.0 cm.
*Height.*—2.0 cm to 3.0 cm.
*Fragrance.*—Absent.

Bracts:
*Number of bracts per inflorescence.*—7 to 8.
*Shape.*—Ovate.
*Apex.*—Acute.
*Base.*—Obtuse.
*Margin.*—Mostly entire.
*Size.*—Length: 7.0 cm to 10.0 cm. Width: 4.0 cm to 8.0 cm.
*Texture (both upper and lower surfaces).*—Smooth.
*Vein color.*—Upper surface: RHS 60A. Lower surface: RHS 53B.
*Bract color.*—Upper surface: RHS 47A. Lower surface: RHS 53B.
*Bract petiole.*—Length: 0.5 cm to 2.0 cm. Diameter: 0.2 cm to 0.3 cm. Color: Upper (part) surface: RHS 53A. Lower (part) surface: RHS 53B.

Cyme:
*Diameter.*—1.0 cm to 2.0 cm.
*Cyathia number.*—5 to 8 per inflorescence.
*Cyathium.*—Shape: Ovate. Diameter: 0.2 cm to 0.5 cm. Length: 0.3 cm to 0.7 cm. Color: RHS 143A.
*Peduncle.*—Color: RHS 142B. Length: 0.2 cm.
*Nectar cups.*—Number: 1 per cyathium. Diameter: 0.1 cm. Size: 0.3 cm to 0.4 cm. Color: RHS 1C.

Reproductive organs:
*Stamens.*—Quantity: 5 to 10 per cyathium. Shape: Ovate.
*Filament.*—Length: 0.25 cm. Color: RHS 46A.
*Pollen.*—Quantity: Moderate. Color: RHS 12A.

Fruit and seed set: Not observed.

Disease and pest resistance: No special disease or pest resistance observed.

COMPARISON WITH PARENTAL LINE AND KNOWN VARIETY

'NPCW14221' is a distinct variety of poinsettia having dark red bracts. 'NPCW14221' is distinguished from its parents as described in Table 1.

TABLE 1

| Characteristic | Variety 'NPCW14221' | Female Parent 'EP-1995-0002' | Male Parent 'EP-1995-0001' |
|---|---|---|---|
| Flowering time | Late | Early | |
| Foliage color | Dark green | | Light green |
| Bract color | Dark red | Medium red | Bright red |

'NPCW14221' can be compared to the commercial poinsettia plant variety 'Duebelita' (U.S. Plant Pat. No. 22,071), also commercially known as 'Bella Italia'. Differences between the two varieties are described in Table 2.

TABLE 2

| Comparison with Similar Variety | | |
|---|---|---|
| Characteristic | 'NPCW14221' | Commercial line 'Duebelita' |
| Vigor | Lower vigor than 'Duebelita' | Higher vigor than 'NPCW14221' |
| Bract size | Smaller bracts than 'Duebelita' | Larger bracts than 'NPCW14221' |
| Number of cyathias | More cyathias than 'Duebelita' | Less cyathias than 'NPCW14221' |

We claim:

1. A new and distinct variety of poinsettia plant named 'NPCW14221' as illustrated and described herein.

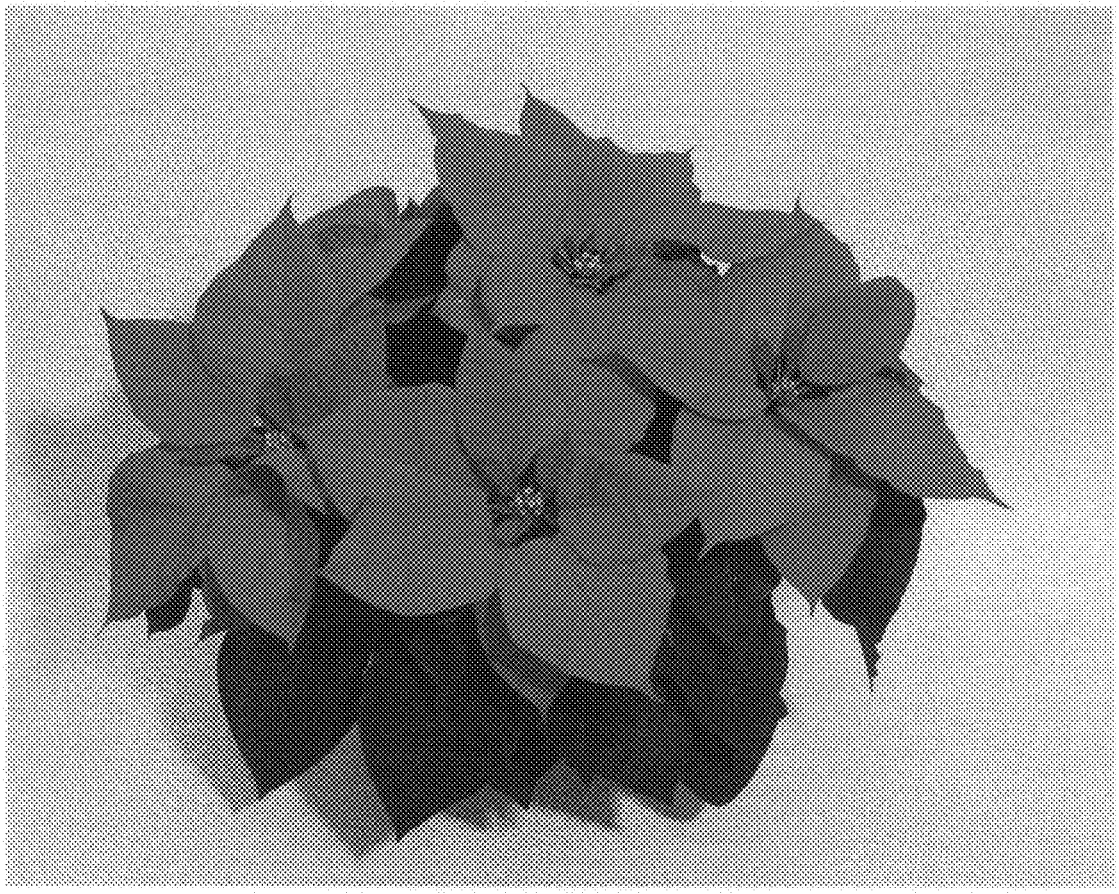

* * * * *